United States Patent

Haddock et al.

[11] Patent Number: 5,653,888
[45] Date of Patent: Aug. 5, 1997

[54] FLUID FILTER ASSEMBLY INCLUDING GEL REMOVING BARBS

[75] Inventors: Thomas F. Haddock; Monty E. Vincent, both of Ann Arbor, Mich.

[73] Assignee: Arbor Technologies, Inc., Ann Arbor, Mich.

[21] Appl. No.: 551,946

[22] Filed: Nov. 2, 1995

[51] Int. Cl.$^6$ .................................. B01D 37/00
[52] U.S. Cl. .................. 210/767; 210/252; 210/259; 210/295; 210/299
[58] Field of Search .................. 210/767, 645, 210/252, 259, 295, 299, 300

[56] References Cited

U.S. PATENT DOCUMENTS

| | | | |
|---|---|---|---|
| 3,935,111 | 1/1976 | Bentley | 210/446 |
| 4,880,548 | 11/1989 | Pall et al. | 210/767 |
| 4,925,572 | 5/1990 | Pall | 210/767 |
| 4,985,153 | 1/1991 | Kuroda et al. | 210/782 |
| 5,190,657 | 3/1993 | Heagle et al. | 210/645 |
| 5,203,778 | 4/1993 | Boehringer et al. | 604/317 |
| 5,252,222 | 10/1993 | Matkovich et al. | 210/650 |

*Primary Examiner*—Robert J. Popovics
*Attorney, Agent, or Firm*—Kohn & Associates

[57] ABSTRACT

A filter assembly (10) includes a housing (12) defining a chamber (14). A filter substrate (16) is disposed within the chamber (14) for filtering fluids passing therethrough. The housing 12 includes an inlet (22) disposed in fluid communication with the chamber (14) for allowing flow of fluid into the chamber (14). The chamber (14) defines a flow path between the inlet (22) and filter substrate (16) for perfecting fluid flow therebetween. An outlet (24) is disposed in fluid communication with the chamber (14) for allowing the flow of fluid to exit the chamber (14). A snagging element (26) is disposed within the housing (14) between the inlet (22) and the filter substrate (16) on the flow path for snagging and retaining gelatinous particulate material from the fluid prior to being filtered. A method of filtering gelatinous material from a flow of fluid includes the steps of snagging gelatinous material from the flowing fluid and then passing the fluid through a filter.

5 Claims, 1 Drawing Sheet

FLUID FILTER ASSEMBLY INCLUDING GEL REMOVING BARBS

TECHNICAL FIELD

This invention relates to a fluid filter device, particularly to a device having utility for filtering fluids requiring removal of gelatinous particulate material from the fluids.

BACKGROUND OF THE INVENTION

It is common practice to filter various kinds of liquids or fluids, such as blood, when the liquids are to be intravenously administered to a patient. Generally the liquid is passed through a filter housing containing a fibrous non-woven bulk media sealed to the walls of the filter housing and supported by a grid or the like.

When dealing with blood filtration, because it is often days or weeks between obtaining a unit of blood and its preparation and infusion into a patient, a variety of blood-specific filtration problems can arise.

Typically, when blood is obtained from a donor to later be used for the purpose of transfusing a recipient, it often sits under refrigeration for several weeks and may develop gelatinous particulate precipitates or materials. Additionally, blood that is collected during surgery from surgical incisions or openings which is to be reinfused back into the patient can also develop gelatinous precipitates which need to be removed prior to the reinfusion of the blood.

The gelatinous materials and other agglomerates, such as fat agglomerates sometimes referred to as a "buffy coat", can range in size from less than 5 microns to up to several millimeters in diameter.

With specific regard to the removal of gelatinous particulate material from blood, the prior art has generally relied upon open-cell lattices such as open-cell foam which trap these gelatinous particulates through size exclusion. Such media suffer from easy blockage by the larger gels which spread out and occlude large areas of the media.

Pall U.S. Pat. No. 4,925,572, issued May 15, 1990, discloses a device for filtering blood products including a gel pre-filter for specifically removing gels present in whole blood samples. The gel pre-filter is formed of a non-woven web or "needled" web formed by passing plastic through a machine fitted with a large number of rapidly reciprocating, multiply barbed needles which randomly engage fibers and pull or push them through the thickness of the web causing the fibers from one face to be pulled to the opposite face where they may become entangled with fibers at that face. The Pall '572 reference discloses that as gel laden blood flows through the needled filter medium, small pores are randomly encountered, and they are sufficient in number to have the net effect of trapping or collecting all or nearly all of the gels within the medium.

Bentley U.S. Pat. No. 3,935,111, issued Jan. 27, 1976, discloses a filter device which removes fat agglomerates from blood utilizing an open-cell foam filter.

Both of the above referenced prior art devices teach the use of either a pre-filter or filter to remove gelatinous particulates from blood. However, because both of these devices remove the gelatinous particulate material either at or directly before the primary filter, these devices are prone to clogging and especially a blockage due to the retention and subsequent spreading out of large gels (a build-up of gelatinous particulate material) of the primary filter and hence the premature failure of the filter.

Therefore, it would be desirable to have a filter assembly which provides for the filtration of gelatinous particulate material from blood wherein the gelatinous particulate material removed does not distinctly reduce or inhibit the functioning of the filter device once it has been removed from the blood.

SUMMARY OF THE INVENTION AND ADVANTAGES

In accordance with the present invention, there is provided a filter assembly including a housing defining a chamber. Filtering means are disposed within the chamber for filtering fluids passing therethrough. The housing includes inlet means disposed in fluid communication with the chamber for allowing flow of fluid into the chamber and outlet means disposed in fluid communication with the chamber for allowing the flow of fluid to exit the chamber. A fluid path is defined by the housing between the inlet means and filtering means. Snagging means are disposed on the flow path within the housing between the inlet means and the filter means for snagging and retaining gelatinous particulate material from the fluid being filtered.

Also in accordance with the present invention, there is provided a method of filtering gelatinous material from a flow of fluid by snagging gelatinous material from the flowing fluid and then passing the fluid through a filter.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
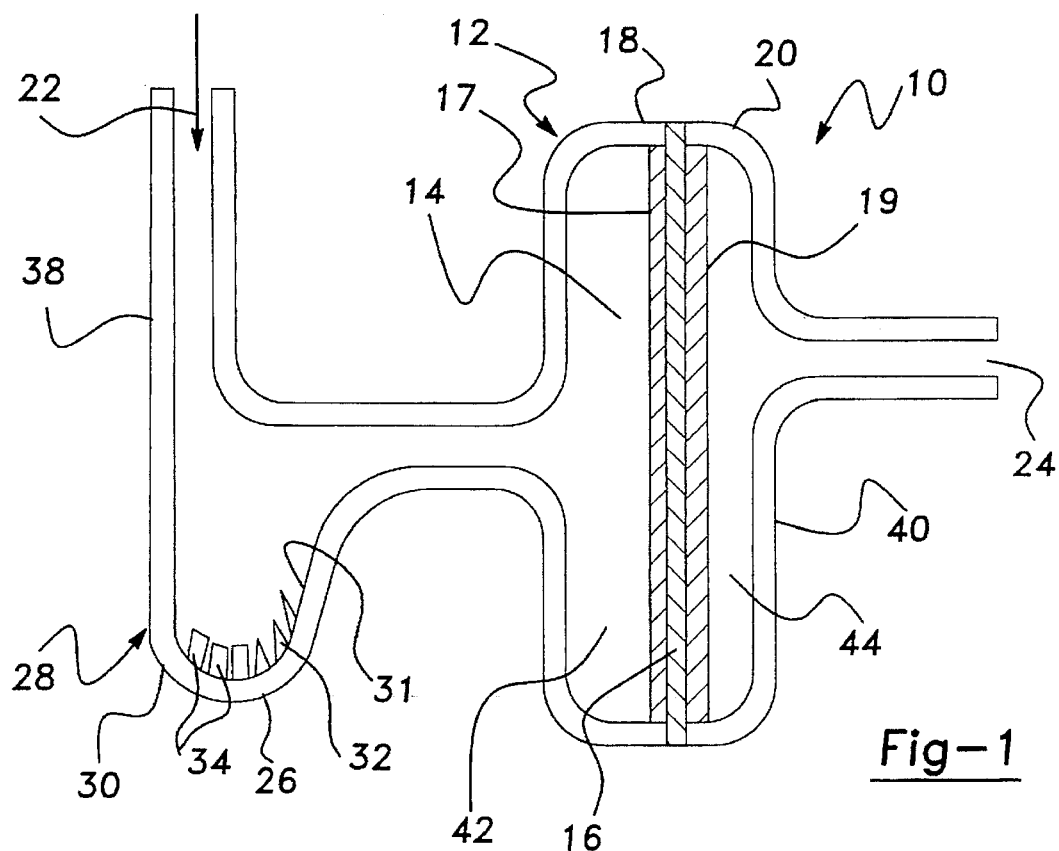
FIG. 1 is a cross-sectional view of the assembly of the present invention wherein the flow of fluid into the filter is perpendicular to the filter.

A filter assembly made in accordance with the present invention is generally shown at 10 in the figures. The filter assembly 10 includes a housing generally shown at 12, the housing 12 having a length extending from a first end 38 to a second end 40. The housing 12 is preferably made from two housing halves 18, 20, the two housing halves 18, 20 defining two walls 18, 20 of the housing 12.

The housing halves 18, 20 can be connected together by means well known in the art such as by gluing, sonic welding, or any other fusion-type bonding, but not limited to these methods. The housing 12 can be constructed of any suitable medical plastic materials, for example polypropylenes, polyolefins, polyesters, polyamides, polycarbonates, polystyrenes, styrenes, co-polymers, and fluoroplastics. This list is not meant to be exhaustive and can include other suitable materials without departing from the present invention.

The filter assembly 10 includes an inlet generally indicated at 22 proximate to the first end 38 of the housing 12, the inlet 22 being in fluid communication with the first chamber 42 for allowing the flow of fluid into the first chamber 42. An outlet is generally shown at 24 as being proximate to the second end 40 of the housing 12 and in fluid communication with the second chamber 44 for allowing a flow of fluid from the second chamber 44 out of the housing 12.

A filter substrate 16 is contained within the housing 12 between the inlet 22 and outlet 24 and separates the housing 12 into first and second chambers 42, 44. The filter substrate 16 can be seated on a grid support 19 of a type well-known in the art. For example, the grid support 19 can be projections or the like extending from an inner surface wherein the projections or the like allow fluid flow through to the second chamber 44. The filter substrate 16 is mounted on an inner surface 31 of the housing 12 about its periphery by means well known in the art. For example, the periphery of the filter substrate 16 can be either heat sealed, glued, or the like to a mounting surface about the periphery of the filter substrate 16. Such means of connecting filter means 16 to filter housing walls 18, 20 are well known in the art.

The filter substrate 16 can include filter media which can be any suitable hydrophobic or hydrophilic material such as cellulose fiber, polysulfones, polyamides, polyolefins, polyesters, and fluoropolymers. This list of materials is not intended to be exhaustive and other suitable materials can be utilized without departing from the present invention.

An optional prefilter 17 constructed of any suitable material such as open-cell foam or cellulose can be included to increase the filtering capacity of the assembly 10 of the present invention.

The inner chambers 42, 44 define a flow path between the inlet 22 and outlet 24 for fluid flow therebetween and through the filter substrate 16.

A snagging mechanism 26 is operatively disposed within the housing 14 between the inlet 22 and the filter substrate 16 along the flow path such that fluid flowing along the flow path comes in contact with the snagging mechanism. The snagging mechanism 26 can include any type of barb, spike, ridge, or the like which is operatively attached at its base to the inner surface 31 of the housing 12.

The snagging mechanism 26 snags, impales, and/or traps gelatinous particulate material from the fluid being passed thereover and retains this material so that it cannot be transported to the primary filtering means 16 where it can cause clogging.

By "snagging", it is meant that the gelatinous particulate material is physically combed or sieved from the flow of fluid passing therethrough and any gelatinous particulate material present in the fluid is removed and settles out of the fluid being filtered. This is as opposed to flow-through size exclusion filtration. "Snagging" also includes the physical retention of the gelatinous particulates by snaring or spearing the gelatinous particulates.

As set forth above, the barbs 32 or ridges 34 which comprise the snagging mechanism 26 are fixedly disposed on the inner surface 31 of the chamber 14 and extend therein.

The snagging mechanism 26 can be disposed adjacent to retention area 28 for retaining the gelatinous material removed from the fluid being filtered. The retention area 28 can include a cavity or depression or basis 30 disposed between the inlet 22 and the filter substrate 16. The base portion of the snagging mechanism 26 is opperatively attached within the cavity 30 by means such as gluing, sonic welding, fusion-type bonding, or the snagging mechanism 26 simultaneously may be formed by extrusion during molding of the housing 12.

The retention area 28, which can include the cavity 30, provides a region where gels which have been snagged from the fluid flowing through the snagging mechanism 26 are allowed to settle by the force of gravity and be retained therein without contaminating or clogging a down stream filter. This area can also be disposed within the cavity 42 so that fluid flow is actually forced over the snagging mechanism 26 and into the retention area 28. This may be accomplished by configuring the housing 10 so that the flow path is directed straight into the retention area 18, as shown in the preferred embodiment. The retention area 28 is preferably located out of the fluid path, however, all or part of the retention area 28 can be located within the fluid path.

In a preferred embodiment of the present invention, the retention area 28 is positioned below the outlet 24 thereby allowing gelatinous material filtered from the fluid to be retained while allowing the fluid to exit through the outlet 24. In other words, the retention area 28 is positioned such that fluid exiting the retention area 28 and entering the first chamber 42 must travel in a direction opposite the force of gravity thereby causing any gelatinous particulate material snagged from the fluid flow to be forced downward with the force of gravity while the filtered fluid flows in an upward direction opposite to that of the gelatinous particulate material further aiding in the separation of gelatinous particulate material from the fluid flow.

Referring to FIG. 1, the filter assembly 10 is shown in which the filter substrate 16 is perpendicularly disposed with respect to the fluid flow. That is, as fluid enters the first chamber 42, it encounters the filter substrate 16 at essentially right angles.

Figure 2:
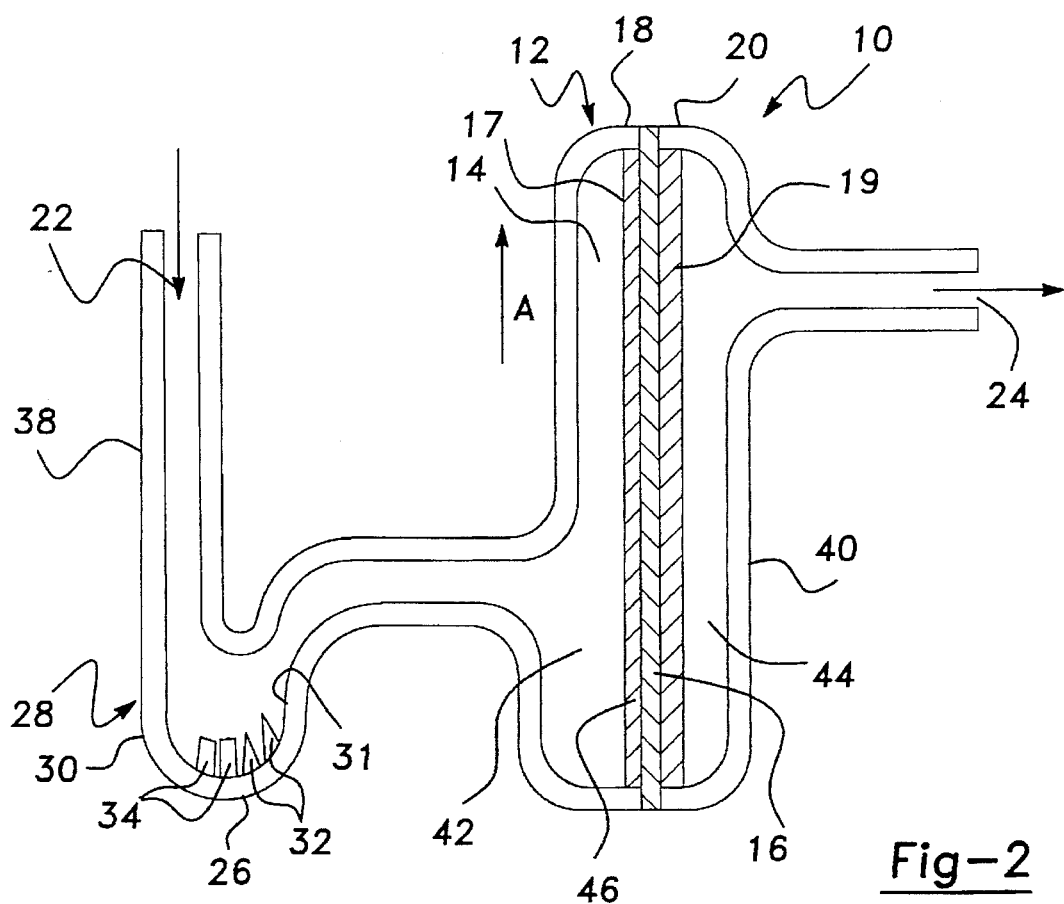
FIG. 2 is a cross-sectional view of a further embodiment of the present invention wherein the flow of the fluid into the filter is semi-tangential to the filter.

Referring to FIG. 2, another preferred embodiment of the present invention is shown. The filter assembly 10 is shown in a configuration in which the filter substrate 16 is tangentially disposed with respect to the fluid flow (denoted by the arrow A). In this embodiment, fluid to be filtered enters through the inlet 22 and travels through the snagging mechanism 26. Following exit from the snagging mechanism 26, the fluid proceeds through the housing 12 and enters the first chamber 42 at a position located at end 46 of the filter substrate 16. As the fluid continues to enter the first chamber 42, the fluid travels upwardly through the filter housing 10 semi-tangentially across the filter substrate 16 in the direction of arrow A. As the fluid flows in this matter, a gradient is formed over the filter mechanism 16 wherein any remaining gelatinous particulate material or other particulate material in the fluid settles in the direction of the end 46 of the filter substrate 16 thereby prolonging the useful life of the filter substrate 16 and the entire apparatus 10 by allowing more of the surface area of the filter substrate 16 to be utilized.

The barbs 32 and/or ridges 34 included in the snagging mechanism 26, preferably range in size from 100's of microns to several mm. The snagging mechanism 26 can be constructed of any suitable medical material, however, the snagging mechanism 26 is preferably constructed of the same material which comprises the housing 12.

The present invention further provides a method of filtering gelatinous material from a flow of fluid by snagging the gelatinous material from the flowing fluid and then passing the fluid through a filter. The fluid can be passed over barbs and/or ridges which retain the gelatinous material.

Throughout this application various patents are referenced. The disclosure of these patents in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

We claim:

1. A filter assembly (10) comprising:

a housing (12) defining a chamber (14);

filtering means (16) disposed within said chamber for filtering fluids passing therethrough;

inlet means (22) disposed in fluid communication with said chamber (14) for allowing flow of fluid into said chamber (14) said housing (12) defining a flow path between said inlet means (22) and filter means (16);

outlet means (24) disposed in fluid communication with said chamber (14) for allowing the flow of the fluid to exit said chamber (14); a cavity (30) disposed between said inlet means (22) and said filter means (16) and snagging means (26) including barbs (32) disposed within said cavity tangentially relative to said flow path between said inlet means (22) and said filter means (16) for snagging and retaining gelatinous particle material tangentially from the fluid prior to being filtered.

2. A filter assembly (10) as set forth in claim 1, wherein said retention means (28) is positioned below said outlet means (24) thereby allowing gelatinous material filtered from the fluid to be retained while allowing the filtered fluid to exit through said outlet means (24).

3. A filter assembly (10) as set forth in claim 1, wherein said filter means (16) is tangentially disposed to the fluid flow.

4. A filter assembly (10) as set forth in claim 1, wherein said filter means (16) is perpendicularly disposed to the fluid flow.

5. A method of filtering a gelatinous material from a flow of fluid said method comprising the steps of:

tangentially flowing fluid over barbs (32) extending from a wall of a filter housing (12) between an inlet (22) and filter (16) of the assembly (10) and snagging gelatinous material on the barbs (32) from the flowing fluid and then passing the fluid through a filter.

* * * * *